(12) United States Patent
Furet et al.

(10) Patent No.: US 9,795,596 B2
(45) Date of Patent: Oct. 24, 2017

(54) PHARMACEUTICAL DIAGNOSTIC

(71) Applicants:Pascal Furet, Thann (FR); Christine Fritsch, Steinbach (FR); Sauveur-Michel Maira, Habsheim (FR)

(72) Inventors: Pascal Furet, Thann (FR); Christine Fritsch, Steinbach (FR); Sauveur-Michel Maira, Habsheim (FR)

(73) Assignee: Novartis AG, Basel (CH)

( * ) Notice: Subject to any disclaimer, the term of this patent is extended or adjusted under 35 U.S.C. 154(b) by 203 days.

(21) Appl. No.: 14/387,653

(22) PCT Filed: Mar. 27, 2013

(86) PCT No.: PCT/EP2013/056600
§ 371 (c)(1),
(2) Date: Sep. 24, 2014

(87) PCT Pub. No.: WO2013/144249
PCT Pub. Date: Oct. 3, 2013

(65) Prior Publication Data
US 2015/0111927 A1    Apr. 23, 2015

Related U.S. Application Data

(60) Provisional application No. 61/617,284, filed on Mar. 29, 2012, provisional application No. 61/767,848, filed on Feb. 22, 2013.

(51) Int. Cl.
*A01N 43/40* (2006.01)
*A61K 31/44* (2006.01)
*A61K 31/4439* (2006.01)
*C12Q 1/68* (2006.01)

(52) U.S. Cl.
CPC ........ *A61K 31/4439* (2013.01); *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,227,462 B2 * | 7/2012 | Fairhurst | C07D 417/14 514/235.8 |
| 8,710,085 B2 * | 4/2014 | Guagnano | C07D 417/14 514/342 |
| 2016/0040255 A1 | 2/2016 | Board et al. | |

FOREIGN PATENT DOCUMENTS

| | | |
|---|---|---|
| CN | 101445832 A | 6/2009 |
| EP | 2377933 A1 | 10/2011 |
| WO | 2010005558 A2 | 1/2010 |
| WO | 2010029082 A1 | 3/2010 |
| WO | 2012/016970 A1 | 2/2012 |

OTHER PUBLICATIONS

Yuan, et. al., Oncogene (2008) 27, 5497-5510.*
Taiwan Medical Journal, 2009, vol. 52, No. 10, pp. 21-24 [English Translation of relevant parts].
"Isoforms selective inhibition of phosphoinositide 3-kinase: Identification of a new region of non-conserved amino acids critical for p110α inhibition", Molecular Pharmacology Fast Forward Published on Jul. 21, 2011.
China Biotechnology, 2009, vol. 29, No. 8, pp. 1-7 [English Translation of relevant parts].
Sabbah Dima A et al: "Biological evaluation and docking studies of recently identified inhibitors of phosphoinositide-3-kinases", Bioorganic & Medicianl Chemistry Letters, 22(2) 876-880 (Jan. 2012).
Frazzetto Mark et al: "Dissecting isoform selectivity of PI3K inhibitors: the role of non-conserved residues in the catalytic pocket", Biochemical Journs, 414(3) 383-390 (Sep. 2008).

* cited by examiner

*Primary Examiner* — Jeffrey H Murray
(74) *Attorney, Agent, or Firm* — Sandra Rueck

(57) ABSTRACT

The present invention relates to selective cancer treatment regimes based on assaying for the presence or absence of a glutamine or a nucleic acid that encodes glutamine at position 859 of the catalytic p110α subunit of PI3K; methods for producing a transmittable form of information for predicting the responsiveness of patient to (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof; and a kit thereof.

2 Claims, 2 Drawing Sheets

PHARMACEUTICAL DIAGNOSTIC

This disclosure claims priority to U.S. Provisional Patent Application No. 61/617,284, filed Mar. 29, 2012, and U.S. Provisional Patent Application No. 61/767,848, filed Feb. 22, 2013, the disclosures of which are each incorporated by reference herein in its entirety.

FIELD OF THE INVENTION

The present invention relates to novel personalized therapies, kits, transmittable forms of information and methods for use in treating patients having cancer.

BACKGROUND OF THE INVENTION

Phosphatidylinositol 3-kinases (PI3Ks) comprise a family of lipid kinases that catalyze the transfer of phosphate to the D-3' position of inositol lipids to produce phophoinositol-3-phosphate (PIP), phosphoinositol-3,4-diphosphate (PIP2) and phosphoinositol-3,4,5-triphosphate (PIP3) that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., Annu. Rev. Biochem 70:535 (2001); Katso et al., Annu. Rev. Cell Dev. Biol. 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one either the p101 or the p84 of two regulatory subunits (Fruman et al., Annu Rev. Biochem. 67:481 (1998); Suire et al., Curr. Biol. 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B, as well as p110β in some circumstances, is activated directly by G protein-coupled receptors that bind a diverse repertoire of peptide and non-peptide ligands (Stephens et al., Cell 89:105 (1997)); Katso et al., Annu. Rev. Cell Dev. Biol. 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., Cell 64:281 (1991); Escobedo and Williams, Nature 335:85 (1988); Fantl et al., Cell 69:413 (1992)).

PIP3 recruits Akt, the product of the human homologue of the viral oncogene v-Aid, to the plasma membrane where it acts as a nodal point for many intracellular signaling pathways important for growth and survival (Fantl et al., Cell 69:413-423(1992); Bader et al., Nature Rev. Cancer 5:921 (2005); Vivanco and Sawyer, Nature Rev. Cancer 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers (Kang at el., Proc. Natl. Acad. Sci. USA 102:802 (2005); Samuels et al., Science 304:554 (2004); Samuels et al., Cancer Cell 7:561-573 (2005)). These observations show that deregulation of phosphoinositol-3 kinase and the upstream and downstream components of this signaling pathway is one of the most common deregulations associated with human cancers and proliferative diseases (Parsons et al., Nature 436:792 (2005); Hennessey at el., Nature Rev. Drug Disc. 4:988-1004 (2005)).

There is an increasing body of evidence that suggests a patient's genetic profile can be determinative to a patient's responsiveness to a therapeutic treatment. Given the numerous therapies available to an individual having cancer, a determination of the genetic factors that influence, for example, response to a particular drug, could be used to provide a patient with a personalized treatment regime. Such personalized treatment regimes offer the potential to maximize therapeutic benefit to the patient while minimizing related side effects that can be associated with alternative and less effective treatment regimes. Thus, there is a need to identify factors which can be used to predict whether a patient is likely to respond to a particular therapeutic therapy.

SUMMARY OF THE INVENTION

The present invention is based on the finding that the identity of the nucleic acid encoding an amino acid at position 859 in the catalytic p110α subunit of PI3K can be used to select individuals having cancer who are likely to respond to treatment with a therapeutically effective amount of an alpha-isoform specific PI3K inhibitor compound such as (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof. Specifically, it was found that an alteration of the glutamine residue (also referred to herein as an Q or Gln) at position 859 in the catalytic p110α subunit of PI3K in a sample from an individual having cancer, can be used to select whether that individual will respond to treatment with alpha-isoform specific PI3K inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof. The determining step can be performed by directly assaying a biological sample from the individual for the subject matter (e.g., mRNA, cDNA, protein, etc.) of interest.

In one aspect, the invention includes a method of selectively treating a subject having cancer, including selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis of the subject having a glutamine at position 859 of the catalytic p110α subunit of PI3K.

In another aspect, the invention includes a method of selectively treating a subject having cancer, including:
a) assaying a biological sample from the subject for the presence or absence of a glutamine at position 859 of the catalytic p110α subunit of PI3K; and b) selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis that the sample has a glutamine at position 859.

In yet another aspect, the invention includes a method of selectively treating a subject having cancer, including either:
a) selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis that the sample has a glutamine at position 859 of the catalytic p110α subunit of PI3K; or
b) selectively administering a therapeutically effective amount of a different PI3K inhibitor compound other than (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) to the subject on the basis that the sample does not have a glutamine at position 859 of the catalytic p110α subunit of PI3K.

In another aspect, the invention includes a method of selectively treating a subject having cancer, including:
assaying a biological sample from the subject for the presence or absence of a glutamine at position 859 of the catalytic p110α subunit of PI3K; and
selectively administering either:
i) a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis that the sample has a glutamine at position 859; or
ii) a therapeutically effective amount of a different PI3K inhibitor compound other than (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) to the subject on the basis that the sample does not have a glutamine at position 859.

In yet another aspect, the invention includes a method of selectively treating a subject having cancer, including:
a) assaying a biological sample from the subject for the presence or absence of glutamine at position 859 of the catalytic p110α subunit of PI3K;
b) thereafter selecting the subject for treatment with (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, on the basis that the subject has a glutamine at position 859 of the catalytic p110α subunit of PI3K; and
c) thereafter administering (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject on the basis that the subject has a glutamine at position 859 of the catalytic p110α subunit of PI3K.

In another aspect, the invention includes a method of selectively treating a subject having cancer, including:
a) determining for the presence or absence of glutamine at position 859 of the catalytic p110α subunit of PI3K in a biological sample from the subject, wherein the presence of glutamine at position 859 indicates that there is an increased likelihood that the subject will respond to treatment with the PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof; and
b) thereafter selecting the subject for treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof on the basis that the sample from the subject has a glutamine at position 859 of the catalytic p110α subunit of PI3K.

In another aspect, the invention includes a method of selecting a subject for treatment having cancer, including determining for the presence or absence of a glutamine at position 859 of the catalytic p110α subunit of PI3K in a biological sample from the subject, wherein the presence of glutamine at position 859 indicates that there is an increased likelihood that the subject will respond to treatment with the PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof.

In another aspect, the invention includes a method of selectively treating a subject having cancer, including selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis of the subject having a nucleic acid sequence that encodes a glutamine at position 859 of the catalytic p110α subunit of PI3K.

In yet another aspect, the invention includes a method of selectively treating a subject having cancer, including:
a) assaying a biological sample from the subject for the presence or absence of nucleic acid sequence mutation at position 2575-2577 of the catalytic p110α subunit of PI3K, compared to a reference sequence; and
b) selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis that the nucleic acid sequence sample has no mutation and encodes a glutamine at position 859.

In yet another aspect, the invention includes a method of selectively treating a subject having cancer, including either:
a) selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis that the subject has a nucleic acid sequence that encodes a glutamine at position 859 of the catalytic p110α subunit of PI3K; or
b) selectively administering a therapeutically effective amount of a different PI3K inhibitor compound to the subject on the basis that the subject has a nucleic acid sequence that does not encode a glutamine at position 859 of the catalytic p110α subunit of PI3K.

In yet another aspect, the invention includes a method of selectively treating a subject having cancer, including:
assaying a biological sample from the subject for the presence or absence of nucleic acid sequence mutation in the catalytic p110α subunit of PI3K, wherein the mutation results in an amino acid substitution of glutamine at position 859 of the catalytic p110α subunit of PI3K; and selectively administering either:
i) a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis that the nucleic acid sequence encodes a glutamine at position 859 in the catalytic p110α subunit of PI3K; or
ii) a therapeutically effective amount of a different PI3K inhibitor compound to the subject on the basis that the nucleic acid sequence has a mutation in catalytic p110α subunit of PI3K at position 859 and does not encode glutamine.

In yet another aspect, the invention includes a method of selectively treating a subject having cancer, including:
a) assaying a biological sample from the subject for the presence or absence of nucleic acid sequence mutation in the catalytic p110α subunit of PI3K, wherein the mutation results in an amino acid substitution of glutamine at position 859 of the catalytic p110α subunit of PI3K;
b) thereafter selecting the subject for treatment with (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, on the basis that the sample from the subject lacks the mutation and encodes glutamine at position 859 of the catalytic p110α subunit of PI3K; and
c) thereafter administering (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject lacking the mutation.

In another aspect, the invention includes method of selectively treating a subject having cancer, including:
a) assaying a biological sample from the subject for the presence or absence of nucleic acid sequence mutation in the catalytic p110α subunit of PI3K, wherein the mutation results in an amino acid substitution of glutamine at position 859 of the catalytic p110α subunit of PI3K, wherein the absence of a mutation in the nucleic acid sequence indicates that there is an increased likelihood that the subject will respond to treatment with the PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof; and
b) thereafter selecting the subject for treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof on the basis that the sample from the subject lacks a mutation in the nucleic acid sequence such that the nucleic acid sequence encodes a glutamine at position 859 of the catalytic p110α subunit of PI3K.

In yet another aspect, the invention includes method of selectively treating a subject having cancer, including:
assaying a nucleic acid sample obtained from the subject having cancer for the presence of a mutation in a nucleic acid molecule encoding the catalytic p110α subunit of the PI3K polypeptide that results in a substitution of glutamine at position 859 of the encoded catalytic p110α subunit;
thereafter either selectively administering:
a) a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, to the subject on the basis that the nucleic acid encodes a glutamine at position 859 of the catalytic p110α subunit of PI3K; or
b) a therapeutically effective amount of a different PI3K inhibitor compound to the subject on the basis that the nucleic acid does not encode a glutamine at position 859 of the catalytic p110α subunit of PI3K.

In another aspect, the invention includes a method of selecting a subject for treatment having cancer, including assaying a nucleic acid sample obtained from the subject having cancer for the presence of a mutation in a nucleic acid molecule encoding the catalytic p110α subunit of the PI3K polypeptide that results in a substitution of glutamine at position 859 of the encoded catalytic p110α subunit, wherein the presence of glutamine at position 859 indicates that there is an increased likelihood that the subject will respond to treatment with the PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof.

In yet another aspect, the invention includes a method of genotyping an individual including detecting a genetic variant at position 859 of the encoded catalytic p110α subunit of PI3K, wherein a lack of variant at position 859 indicates that (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) should be administered to the individual.

In yet another aspect, the invention includes a method of genotyping an individual including detecting for the absence or presence of CAA at position 2575-2577 in the catalytic p110α subunit of PI3K gene obtained from said individual, wherein the presence of CAA indicates the individual has an increased likelihood of responding to (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide).

Also in the methods of the invention as described herein the cancer can be any cancer including glioblastoma; melanoma; ovarian cancer; breast cancer; non-small-cell lung cancer (NSCLC); endometrial cancer, prostate cancer; colon cancer; and myeloma. Typically, the sample is a tumor sample and can be a fresh frozen sample or a parrafin embedded tissue sample.

In the methods of the invention as described herein, methods of detecting glutamine or a variant amino acid can be preformed by any method known in the art such as immunoassays, immunohistochemistry, ELISA, flow cytometry, Western blot, HPLC, and mass spectrometry. In addition, in the methods of the invention as described herein, methods for detecting a mutation in a nucleic acid molecule encoding the catalytic p110α subunit of the PI3K include polymerase chain reaction (PCR), reverse transcription-polymerase chain reaction (RT-PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperature gradient gel electrophoresis (TGGE), denaturing high performance liquid chromatography, high-resolution melting analysis, DNA mismatch-binding protein assays, SNPLex®, or capillary electrophoresis, The invention further includes a method for producing a transmittable form of information for predicting the responsiveness of a patient having cancer to treatment with (S)-

Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), comprising:
a) determining whether a subject has an increased likelihood that the patient will respond to treatment with (S)-Pyrrolidine-1,2-dicarboxylic acid 2-amide-1-({4-methyl-5-[2-(2,2,2-trifluoro-1,1-dimethyl-ethyl)-pyridin-4-yl]-thiazol-2-yl}-amide), wherein the subject has an increased likelihood based on having a glutamine at position 859 of the catalytic p110α subunit gene of PI3K, and
b) recording the result of the determining step on a tangible or intangible media form for use in transmission.

In another aspect, the invention includes a method for producing a transmittable form of information for predicting the responsiveness of a patient having cancer to treatment with (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), including:
a) determining whether a subject has an increased likelihood that the patient will respond to treatment with (S)-Pyrrolidine-1,2-dicarboxylic acid 2-amide-1-({4-methyl-5-[2-(2,2,2-trifluoro-1,1-dimethyl-ethyl)-pyridin-4-yl]-thiazol-2-yl}-amide), wherein the subject has an increased likelihood based on the nucleic acid sequence encoding a glutamine at position 859 of the catalytic p110α subunit gene of PI3K; and
b) recording the result of the determining step on a tangible or intangible media form for use in transmission.

In yet another aspect, the invention includes a kit for determining if a tumor is responsive for treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof comprising providing one or more probes or primers for detecting the presence of a mutation at the PI3K gene locus (nucleic acid 2575-2577 of SEQ ID NO:2) and instructions for use.

In another aspect, the invention includes a kit for predicting whether a subject with cancer would benefit from treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, the kit comprising:
    a) a plurality of agents for determining for the presence of a mutation that encodes a variant at position 859 of the catalytic p110α subunit of PI3K; and
    b) instructions for use.

In the methods of the invention as described herein, the PI3K inhibitor is any known PI3K alpha subunit inhibitor in the art. In particular the compound can be (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof; shown also below as formula (A)

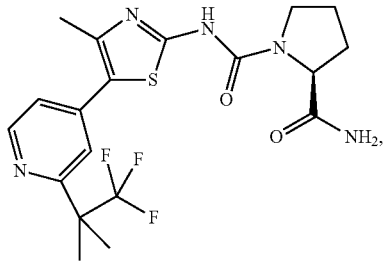

(A)

or a pharmaceutically acceptable salt thereof.

In another aspect, the invention includes a kit for determining if a tumor is responsive for treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof comprising providing one or more probes or primers for detecting the presence or absence of a mutation that encodes a variant in the catalytic p110α subunit of the PI3K gene at position 859.

DETAILED DESCRIPTION OF THE INVENTION

Figure 1:
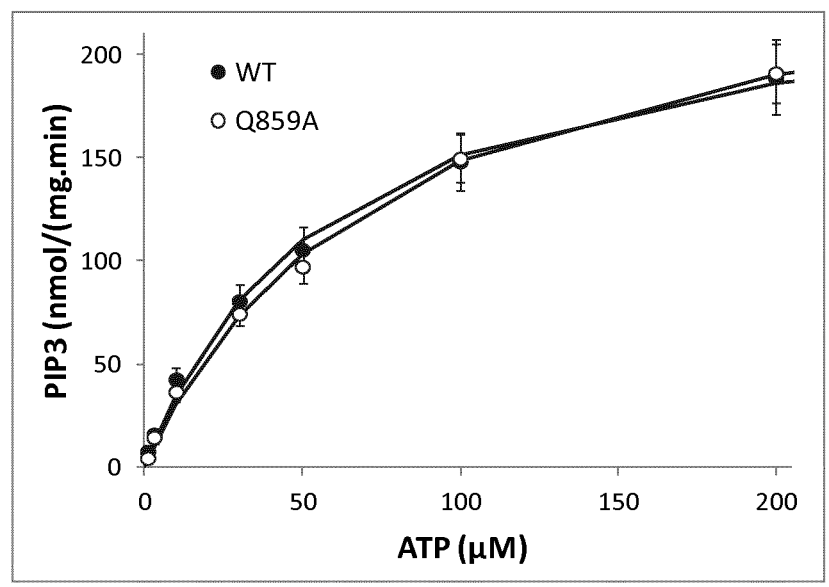
FIG. 1 depicts a graph showing ATP activation kinetics curves for PI3K wild-type (wt) (Michaelis constant (Km) =60±6 µM) and for PI3Kα Q859A mutant (Km=72±8 µM).

The present invention is based on the finding that the presence or absence of a mutation in a nucleic acid sequence encoding a glutamine at position 859 of the catalytic p110α subunit of PI3K can be used to determine the likelihood of response of a patient to therapy with an alpha-isoform specific PI3K inhibitor compound such as (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof. Specifically, it was found that a nucleic acid sequence from patient's sample that encodes the wild type catalytic p110α subunit of PI3K, i.e., has a glutamine at position 859, is more likely to respond to treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide). In contrast, a nucleic acid sequence from a patient's sample having a mutation that encodes a variant at position 859 of the catalytic p110α subunit of PI3K, i.e., encodes an amino acid other than a glutamine at position 859, such as an alanine, is less likely to respond to treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide). Such a patient should be treated with an alternative cancer therapy such as a different PI3K inhibitor (as used herein different type of PI3K inhibitor should be an inhibitor which is not (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), and can be, but not limited to, treatment with a chemotherapeutic or an alternate PI3K inhibitor therapy such as an inhibitor that can selectively inhibit an isoform other than the alpha form of the PI3K subunit or an inhibitor that can inhibit more than one isoform of the PI3K subunit.

In some embodiments of the methods of the invention, the presence or absence of a mutation in a nucleic acid sequence that encodes glutamine at position 859 in the catalytic p110α subunit of PI3K, may be detected by assaying the biological sample for a genomic sequence, a nucleic acid product, a polypeptide product, or an equivalent genetic marker.

In one example, the invention includes genotyping a sample from an individual. For genotyping the nucleotide characters that encode glutamine at position 859 are determined in either one allele or both alleles of the catalytic p110α subunit of PI3K gene. With respect to catalytic p110α subunit of PI3K gene, the mutation occurs at nucleotide 2575-2577 of catalytic p110α subunit of PI3K gene in one or both alleles. A genotype can be homozygous or heterozygous. In the methods of the invention, the determination of the identity of the nucleic acid sequence, or protein, at position 859 can be compared to the wild-type protein sequence (GeneID: 5290; encoding, for example, a protein with NCBI Accession number NP_006209.2; SEQ ID NO:1) or DNA sequence (SEQ ID NO:2) or wild-type nucleic acid sequence (mRNA; NCBI Reference Sequence number NM_006218.2) or genomic DNA (NCBI Reference Sequence number NG_012113.1), as appropriate. A variant at position 859 (i.e., an amino acid other than glutamine) of the catalytic p110α subunit of PI3K is used to refer to a change in the reference (wildtype) protein sequence at position 859 resulting from a genetic mutation in the catalytic p110α subunit of PI3K gene sequence which encodes the protein. In one embodiment, the variant can be an alanine at position 859.

The present disclosure thus provides methods to predict the likelihood that a patient having a PI3K-expressing cancer will exhibit a beneficial response to a therapy with the PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof. Patients subject to such an assessment include: 1) patients who have a PI3K-expressing cancer and who have not yet undergone any treatment for the cancer; 2) patients who have a PI3K-expressing cancer and who have undergone complete or partial resection of the cancer, e.g., who have undergone surgical removal of cancerous tissues to the extent clinically possible; and 3) patients who have a PI3K-expressing cancer and who have been treated with a treatment regimen other than a PI3K inhibitor treatment regimen.

In the methods of the invention, a sample is assayed for the presence or absence of a mutation encoding a glutamine at position 859 of the catalytic p110α subunit of PI3K gene PIK3CA. In one example, the mutation results in a substitution/variant of a glutamine for an alanine at position 859 in the human catalytic p110α subunit of the PI3K gene PIK3CA (Q859A) [GeneID: 5290; encoding, for example, a protein with NCBI Accession number NP_006209.2 (SEQ ID NO: 1).

In one aspect, the invention includes a method of selectively treating a subject having cancer including assaying a biological sample from the subject for the presence or absence of a glutamine at position 859 of the catalytic p110α subunit of PI3K; and selectively administering PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject on the basis that the sample has a glutamine at position 859.

In another aspect, the invention includes a method of selectively treating a subject having cancer including assaying a biological sample from the subject for the presence or absence of a mutation that encodes a variant at position 859 of the catalytic p110α subunit of PI3K; and selectively administering PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject on the basis that the sample from the subject lacks a mutation at position 859 of the catalytic p110α subunit of PI3K.

In another aspect, the invention includes a method of selectively treating a subject having cancer including assaying a biological sample from the subject for the presence or absence of a mutation that encodes a variant at position 859 of the catalytic p110α subunit of PI3K; thereafter selecting the subject for treatment with the PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof on the basis that the sample from the subject lacks a mutation at position 859 of the p110α subunit of the catalytic p110α subunit of PI3K (i.e., the nucleic acid sequence encodes a glutamine); and administering PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject as a result of the subject lacking the mutation.

In yet another aspect, the invention includes a method of selectively treating a subject having cancer including determining for the presence or absence of a mutation that encodes a variant at position 859 of the catalytic p110α subunit of PI3K in a biological sample from the subject, wherein the presence of a mutation indicates that there is an increased likelihood that the subject will not respond to treatment with the PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof; and thereafter selecting the subject for treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof on the basis that the sample from the subject lacks a mutation at position 859 of the catalytic p110α subunit of the p110α subunit of PI3K.

In still yet another aspect, the invention includes a method of selectively treating a subject having cancer with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof including administering PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject on the basis that the subject has the presence of a glutamine (Q) at position 859 of the catalytic p110α subunit of PI3K.

In still yet another aspect, the invention includes a method of selectively treating a subject having cancer including assaying a nucleic acid sample obtained from the subject having cancer for the presence of one or more mutations in a nucleic acid molecule at positions 2575-2577 of the catalytic p110α subunit of the PI3K polypeptide; and thereafter selectively administering a PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject on the basis that the subject lacks the presence of a sequence mutation and encodes a glutamine at position 859 of the encoded catalytic p110α subunit of PI3K.

In still another aspect, the invention includes a PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof for use in treating cancer, characterized in that a therapeutically effective amount of said compound or its pharmaceutically acceptable salt is administered to the patient on the basis of said patient having a glutamine at position 859 of the catalytic p110α subunit of PI3K.

In still another aspect, the invention includes a PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof for use in treating cancer, characterized in that a therapeutically effective amount of said compound or its pharmaceutically acceptable salt is administered to the patient on the basis of said patient having a glutamine at position 859 of the catalytic p110α subunit of PI3K selected from a glutamine at position 859 of the catalytic p110α subunit of PI3K and not having a glutamine at position 859 of the catalytic p110α subunit of PI3K.

In still another aspect, the invention includes a PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof for use in treating cancer, characterized in that a therapeutically effective amount of said compound or its pharmaceutically acceptable salt is administered to the patient on the basis of said patient having nucleic acid encoding a glutamine at position 859 of the catalytic p110α subunit of PI3K.

In still another aspect, the invention includes a PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof for use in treating cancer, characterized in that a therapeutically effective amount of said compound or its pharmaceutically acceptable salt is administered to the patient on the basis of said patient having nucleic acid encoding a glutamine at position 859 of the catalytic p110α subunit of PI3K selected from a nucleic acid encoding a glutamine at position 859 of the catalytic p110α subunit of PI3K and a nucleic acid encoding not encoding a glutamine at position 859 of the catalytic p110α subunit of PI3K.

PI3K Inhibitors

A patient being assessed using the method disclosed herein is one who is being considered for treatment with a PI3K inhibitor. According to the present invention patients having tumors which express a wild type form of the catalytic p110α subunit of PI3K are more likely to respond to treatment with PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof.

As used herein, the term "PI3K alpha subunit inhibitor" is a molecule that can inhibit the catalytic p110α subunit of PI3K. It is understood that a PI3K alpha subunit inhibitor can selectively inhibit the alpha subtype of PI3K as compared to its ability to inhibit the other subtypes including beta and/or delta and/or gamma subtypes.

WO2010/029082 describes specific 2-carboxamide cycloamino urea derivatives, which have been found to have advantageous pharmacological properties and show an improved selectivity for the PI3-kinase alpha subtype as compared to other types. Specific 2-carboxamide cycloamino urea derivatives which are suitable for the present invention, their preparation and suitable formulations containing the same are described in WO2010/029082. In the methods of the invention as described herein, the PI3K alpha subunit inhibitor can be a compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof. The PI3K alpha subunit inhibitor used in the present invention is a compound of formula (A)

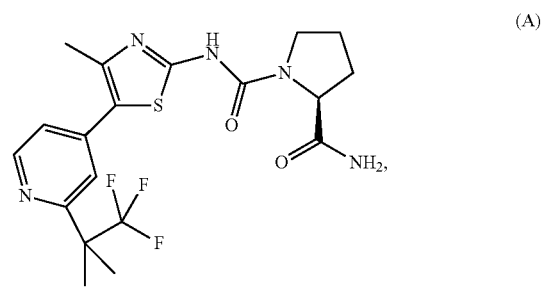 [SMILES: Cc1nc(NC(=O)N2CCC[C@H]2C(N)=O)sc1-c1ccnc(C(C)(C)C(F)(F)F)c1]

(A)

or a pharmaceutically acceptable salt thereof. This compound is specifically described in WO2010/029082. The synthesis of this compound is described in WO2010/029082 as Example 15.

The PI3K alpha subunit inhibitor compound described herein can be the agent itself, a pharmaceutically acceptable salt thereof, a pharmaceutically acceptable ester thereof, as well as a stereoisomer, enantiomer, racemic mixture, and the like.

Preparation of Samples

The invention provides, among other things, an assay for the detection of the identity of the nucleic acid sequence that encodes amino acid 859 of the catalytic p110α subunit of PI3K. If the nucleic acid encodes the wildtype amino acid glutamine this is indicative that the subject should be selected and treated with a PI3K alpha subunit inhibitor compound (as above). However, if the nucleic acid has a mutation and encodes a variant amino acid, i.e., encodes an amino acid other than glutamine, then the subject should not be treated with a PI3K alpha subunit inhibitor compound (as above).

The method can include detecting the mutation in a body fluid such as blood (e.g., serum or plasma) bone marrow, cerebral spinal fluid, peritoneal/pleural fluid, lymph fluid, ascite, serous fluid, sputum, lacrimal fluid, stool, and urine, or in a tissue such as a tumor tissue. The tumor tissue can be fresh tissue or paraffin-embedded tissue.

As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model.

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, acellular DNA in a body fluid sample is separated from cells, precipitated in alcohol, and dissolved in an aqueous solution.

Generally, a solid tumor sample can be test sample of cells or tissue that are obtained from a subject with cancer by biopsy or surgical resection. A sample of cells or tissue can be removed by needle aspiration biopsy. For this, a fine needle attached to a syringe is inserted through the skin and into the tissue of interest. The needle is typically guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue can also be removed by incisional or core biopsy. For this, a cone, a cylinder, or a tiny bit of tissue is removed from the region of interest. CT imaging, ultrasound, or an endoscope is generally used to guide this type of biopsy. More particularly, the entire cancerous lesion may be removed by excisional biopsy or surgical resection. In the present invention, the test sample is typically a sample of cells removed as part of surgical resection.

The test sample of, for example tissue, may also be stored in, e.g., RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. RNA or protein may also be extracted from a fixed or wax-embedded tissue sample.

PI3K-expressing cancers useful for treatment according to the present invention include cancers or cellular proliferative diseases such as tumor and/or cancerous cell growth mediated by PI3K. Diseases may include those showing overexpression or amplification of PI3K alpha, somatic mutation of PIK3 CA or germline mutations or somatic mutation of PTEN or mutations and translocation of p85α that serve to up-regulate the p85-p110 complex. In particular, cancer includes, for example, sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia vera; essential thrombocythemia; myelofibrosis with myeloid metaplasia; and Walden-stroem disease.

The method of the invention is not limited to cancers and can include other conditions or disorders (e.g. PI3K-mediated) such as polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

Detection

The methods of the invention include detecting for the presence or absence of a mutation in the nucleic acid sequence that encodes the amino acid glutamine at position 859 of the human p110α subunit of the PI3K gene. In one example, this method includes detecting a nucleic acid encoding a mutated amino acid at position 859 to predict the response of a patient to a PI3K drug treatment. Since mutations in the catalytic p110α subunit of the PI3K generally occur at the DNA level, the methods of the invention can be based on detection of mutations in genomic DNA, as well as transcripts (mRNA, cDNA) and proteins themselves.

The PI3K catalytic p110α subunit mutations described herein can be detected by any known method in the art. In describing the PI3K catalytic p110α subunit mutation of the invention the mutation includes any amino substitution of the glutamine (Q) amino acid that exists in the wild type sequence at position 859, for example, the substitution can be a glutamine (Q) for an alanine (A). In addition the PI3K catalytic p110α subunit mutation referred to herein is to the sense strand of the gene for convenience. As recognized by the skilled artisan, however, nucleic acid molecules containing the gene may be complementary double stranded molecules and thus reference to a particular site on the sense strand refers as well to the corresponding site on the complementary antisense strand. That is, reference may be made to the same mutant site on either strand and an oligonucleotide may be designed to hybridize specifically to either strand at a target region containing the polymorphic and/or mutant site. Thus, the invention also includes single-stranded polynucleotides and mutations that are complementary to the sense strand of the genomic variants described herein.

Many different techniques can be used to identify if the nucleic acid sequence encodes a mutation at position 859 in the catalytic p110α subunit of PI3K including single-strand conformation polymorphism (SSCP) analysis, heteroduplex analysis by denaturing high-performance liquid chromatography (DHPLC), direct DNA sequencing and computational methods (Shi et al, Clin Chem A1U6AA12 (2001)). The most common methods currently include hybridization, primer extension, and cleavage methods. Each of these methods must be connected to an appropriate detection system. Detection technologies include fluorescent polarization (Chan et ah, Genome Res. 9:492-499 (1999)), luminometric detection of pyrophosphate release (pyrosequencing) (Ahmadiian et ah, Anal. Biochem. 280:103-10 (2000)), fluorescence resonance energy transfer (FRET)-based cleavage assays, DHPLC, and mass spectrometry (Shi, Clin Chem 47:164-172 (2001); U.S. Pat. No. 6,300,076 B1).

In one embodiments, an automatic analyzer (e.g., a PCR machine or an automatic sequencing machine) is used to determine the presence or absence of a mutation at position 2575 to 2577 (codon that encodes Gln at position 859) in the catalytic p110 alpha subunit of PI3K. All such methods are well known by skilled artisans.

In a particularly preferred embodiment, mutations can be detected using INVADER™ technology (available from Third Wave Technologies Inc. Madison, Wis. USA). In this assay, a specific upstream "invader" oligonucleotide and a partially overlapping downstream probe together form a specific structure when bound to complementary DNA template. This structure is recognized and cut at a specific site by the Cleavase enzyme, resulting in the release of the 5' flap of the probe oligonucleotide. This fragment then serves as the "invader" oligonucleotide with respect to synthetic secondary targets and secondary fluorescently labelled signal probes contained in the reaction mixture. This results in specific cleavage of the secondary signal probes by the Cleavase enzyme. Fluorescent signal is generated when this secondary probe (labelled with dye molecules capable of fluorescence resonance energy transfer) is cleaved. Cleavases have stringent requirements relative to the structure formed by the overlapping DNA sequences or flaps and can, therefore, be used to specifically detect single base pair mismatches immediately upstream of the cleavage site on the downstream DNA strand. Ryan D et ah, Molecular Diagnosis 4(2): 135-144 (1999) and Lyamichev V et ah. Nature Biotechnology 17: 292-296 (1999), see also U.S. Pat. Nos. 5,846,717 and 6,001,567.

The invention further includes compositions which contain oligonucleotide probes and primers designed to specifically hybridize to the nucleic acid sequence that encodes glutamine or a variant polypeptide at position 859 of the catalytic p110α subunit, or that are adjacent to a mutant site. The region containing the mutation of interest can be amplified using any oligonucleotide-directed amplification method, including but not limited to polymerase chain reaction (PCR). (U.S. Pat. No. 4,965,188), ligase chain reaction (LCR) (Barany et al, Proc. Natl. Acad. ScL USA 88:189-193 (1991); published PCT patent application WO 90/01069), and oligonucleotide ligation assay (OLA) (Landegren et al, Science 241: 1077-1080 (1988)). Oligonucleotides useful as primers or probes in such methods should specifically hybridize to a region of the nucleic acid that contains or is adjacent to the polymorphic/mutant site. Typically, the oligonucleotides, are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the region containing the catalytic p110α subunit mutation at position 859 includes transcription-based amplification systems (U.S. Pat. No. 5,130,238; EP 329,822; U.S. Pat. No. 5,169,766, published PCT patent application WO 89/06700) and isothermal methods. (Walker et al., Proc. Natl. Acad. Sci. USA 89: 392-396 (1992)).

A mutation at position 859 of the catalytic p110α subunit may be assayed before or after amplification using one of several hybridization-based methods known in the art. Typically, allele-specific oligonucleotides are utilized in performing such methods. The allele-specific oligonucleotides may be used as differently labelled probe pairs, with one member of the pair showing a perfect match to one variant of a target sequence and the other member showing a perfect match to a different variant. Preferably, the members of the set have melting temperatures within 5 Degrees centigrade and more preferably within 2 degrees centigrade, of each other when hybridizing to each of the polymorphic or mutant sites being detected. Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking, baking, etc. Allele-specific oligonucleotide may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibres, chips, dishes, and beads. The solid support may be treated, coated or derivatised to facilitate the immobilization of the allele-specific oligonucleotide or target nucleic acid.

Polypeptides having a glutamine at position 859 or having a substitution at position 859 of the catalytic p110 subunit can also be assayed using methods known in the art, such as radioimmunoassays or enzyme-linked immunoassays, competitive binding enzyme-linked immunoassays, mass spectrometry, point of care techniques/platforms, dot blot, Western blot, chromatography, preferably high performance liquid chromatography (HPLC), or the like. Labeled antibodies, binding portions thereof, or other binding partners can be used. The antibodies can be monoclonal or polyclonal in origin, or may be biosynthetically produced. The binding partners may also be naturally occurring molecules or synthetically produced. The amount of complexed proteins is determined using standard protein detection methodologies described in the art. A detailed review of immunological assay design, theory and protocols can be found in numerous texts in the art, including Practical Immunology, Butt, W. R., ed., Marcel Dekker, New York, 1984.

A variety of different labels can be used in the assays of the invention including direct labels such as fluorescent or luminescent tags, metals, dyes, radionuclides, and the like, attached to the antibody. Indirect labels include various enzymes well known in the art, such as alkaline phosphatase, hydrogen peroxidase and the like. In a one-step assay, the target protein (i.e., the catalytic p110 subunit having a glutamine at position 859) is immobilized and incubated with a labeled antibody. The labeled antibody binds to the immobilized target molecule. After washing to remove unbound molecules, the sample is assayed for the presence of the label. Numerous immunohistochemical methods are incorporated into point-of-care formats and hand-helds, all of which may be used for determine presence of the protein.

The use of immobilized antibodies specific for the proteins or polypeptides is also contemplated by the present disclosure. The antibodies can be immobilized onto a variety of solid supports, such as magnetic or chromatographic matrix particles, the surface of an assay place (such as microtiter wells), pieces of a solid substrate material (such as plastic, nylon, paper), and the like. An assay strip can be prepared by coating the antibody or a plurality of antibodies in an array on solid support. This strip can then be dipped into the test sample and processed through washes and detection steps to generate a measurable signal, e.g., a colored spot.

In a two-step assay, an immobilized target protein (e.g., the catalytic p110 subunit having a glutamine at position 859) may be incubated with an unlabeled antibody. The unlabeled antibody complex, if present, is then bound to a second, labeled antibody that is specific for the unlabeled antibody. The sample is washed and assayed for the presence of the label. The choice of marker used to label the antibodies will vary depending upon the application. However, the choice of the marker is readily determinable to one skilled in the art.

Dot blotting is routinely practiced by the skilled artisan to detect a desired protein using an antibody as a probe (Promega Protocols and Applications Guide, Second Edition, 1991, Page 263, Promega Corporation). Samples are applied to a membrane using a dot blot apparatus. A labeled probe is incubated with the membrane, and the presence of the protein is detected.

Western blot analysis is well known to the skilled artisan (Sambrook et al., Molecular Cloning, A Laboratory Manual, 1989, Vol. 3, Chapter 18, Cold Spring Harbor Laboratory). In Western blot, the sample is separated by SDS-PAGE. The gel is transferred to a membrane. The membrane is incubated with labeled antibody for detection of the desired protein.

Administration and Pharmaceutical Compositions

The PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof can be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For the above uses the required dosage will of course vary depending on the mode of administration, the particular condition to be treated and the effect desired.

In general, for satisfactory results are indicated to be obtained systemically at daily dosages of from about 0.03 to about 100.0 mg/kg per body weight, e.g. about 0.03 to about 10.0 mg/kg per body weight of the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof. An indicated daily dosage in the larger mammal, e.g. humans, is in the range from about 0.5 mg to about 3 g, e.g. about 5 mg to about 1.5 g of the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, conveniently administered, for example, in divided doses up to four times a day or in retard form. Suitable unit dosage forms for oral administration comprise from ca. 0.1 to about 500 mg, e.g. about 1.0 to about 500 mg of the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof.

The PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof as described herein can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising the PI3K alpha subunit inhibitor compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or poly ethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions.

The PI3K alpha subunit inhibitor compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Data

In performing any of the methods described herein that require determining the presence or absence of a nucleic acid mutation at position 2575-2577 of the p110 catalytic subunit of PI3K, are determined, and physicians or genetic counselors or patients or other researchers may be informed of the result. Specifically the result can be cast in a transmittable form of information that can be communicated or transmitted to other researchers or physicians or genetic counselors or patients. Such a form can vary and can be tangible or intangible. The result can be embodied in descriptive statements, diagrams, photographs, charts, images or any other visual forms. For example, images of gel electrophoresis of PCR products can be used in explaining the results. Diagrams showing a variant is present or absent are also useful in indicating the testing results. These statements and visual forms can be recorded on a tangible media such as papers, computer readable media such as floppy disks, compact disks, etc., or on an intangible media, e.g., an electronic media in the form of email or website on internet or intranet. In addition, the result can also be recorded in a sound form and transmitted through any suitable media, e.g., analog or digital cable lines, fiber optic cables, etc., via telephone, facsimile, wireless mobile phone, internet phone and the like. All such forms (tangible and intangible) would constitute a "transmittable form of information". Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present disclosure also encompasses a method for producing a transmittable form of information containing data on whether a mutation occurs at position 859 of the p110 catalytic domain in an individual. This form of information is useful for predicting the responsiveness of a patient to treatment with at PI3K inhibitor, for selecting a course of treatment based upon that information, and for selectively treating a patient based upon that information.

Kits

The invention further provides kits for determining whether a mutation exists at position 2575-2577 of a human catalytic p110α subunit of the PI3K gene. The kits are useful for selecting patients who will specifically benefit from treatment with PI3K alpha subunit inhibitor compound (S)-Pyrrolidine-1,2-dicarboxylic acid 2-amide-1-({4-methyl-5-[2-(2,2,2-trifluoro-1,1-dimethyl-ethyl)-pyridin-4-yl]-thiazol-2-yl}-amide) or a pharmaceutically acceptable salt thereof. A kit can comprise primers and/probes useful for detecting a mutation at position 859 of the human catalytic p110α subunit of the PI3K gene. A kit may further comprise nucleic acid controls, buffers, and instructions for use.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

Example 1: Materials and Methods for Cloning and Expression of Catalytic p110α Wild-Type and Mutant Q859A with p85 Isoform 1

DNA Handling and Plasmids:

Standard molecular biology techniques are used to construct the plasmids described. All enzymes are obtained from Roche Diagnostics and New England BioLabs. DNA fragments are either purified using the GenElute PCR Cleanup kit (Sigma) or are isolated from preparative agarose gels with the Nucleospin Extract II (Macherey-Nagel). DNA-ligations are conducted for 1 to 4 hours at room temperature with the Rapid DNA Ligation kit (Roche Diagnostics) and are transformed into E. coli DH5 alpha (Invitrogen). Plasmid DNA is purified with the QIAprep 8 Miniprep Kit (QIAGEN) or the GenElute HP Plasmid Midiprep Kit (Sigma). All procedures are conducted as described in the respective manuals.

The plasmid His-Nativ hPI3k-alpha/p85 pDUAL Consensus is prepared. For this construct, bovine a 3243 bp DNA fragment containing the entire open reading frame of the bovine PI3-K p110α isoform (RefSeq NM_174574.1) is amplified by PCR from a plasmid provided by Matthias Wymann (Institute of Biochemistry, University of Freibourg) using the GATEWAY compatible primers shown in Table 1. Briefly, the forward primer PI3Ka_FOR_GATE contained a BamH I restriction site (single underline), Kozak recognition site (double underline) and the attB1 sequence required for GATEWAY cloning (italics), whilst the reverse primer PI3_Ka_REV_GATE contained a Hind III restriction site (single underline) and attB2 GATEWAY sequence (italics). PCR amplifications were performed using High Fidelity Platinum Pfx DNA polymerase (Invitrogen) following the manufacturer's protocols.

TABLE 1

Primers used for bovine PI3-Kα PCR Amplification

| Primer Name | Primer Sequence |
| --- | --- |
| PI3_Ka_FOR_GATE | GGGG ACA AGT TTG TAC AAA AAA GCA GGC TGG GGATCC ACC ATG CCT CCA AGA CCA TCA TCA GGT GAA CTG (SEQ ID NO: 3) |
| PI3_Ka_REV_GATE | GGGG AC CAC TTT GTA CAA GAA AGC TGG GTG AAGCTT TCA GTT CAA AGC ATG CTG CTT AAT (SEQ ID NO: 4) |

Following PCR, fragments are purified using 30% PEG 8000; 30 mM MgCl2 to remove attB primer dimers, and are transposed into the GATEWAY entry vector pDONOR 201. Briefly, 4 μL pf PCR product (10 ng/μL) is mixed with 2 μL Reaction Mix, 1 μL pDONOR 201 (150 ng/L), 2 μL BP Clonase and 1 μL TE and is incubated at room temperature for 60 minutes before addition of 2 μL of Proteinase K (2 μg/μL). Samples are then incubated for a further 60 minutes at 37° C. and then are used to transform DH5α competent cells. Positive recombinant PI3-Kα pDONOR plasmids are subsequently identified by restriction enzyme analysis and are sequence verified (SOLVIAS). 2 μL of freshly prepared PI3-Kα pDONOR is then mixed with 2 μL of pDEST 20 (150 ng/μL), 2 μL Reaction Mix, 2 μL LR Clonase and 2 μL TE. Samples are incubated at room temperature as described above before transformation of DH5α competent cells to create GST-PI3-Kα pDEST 20.

A 3933 bp PCR product containing the entire open reading frame of GST-PI3-Kα is then amplified using gene specific oligonucleotides containing Spe I and Hind III (underlined) flanking sites (Table 2) from GST-PI3-Kα pDEST 20 and ligated into p50 pFastBac DUAL as described above.

TABLE 2

Primers used for GST-PI3-Kα PCR Amplification

| Primer Name | Primer Sequence |
| --- | --- |
| GST-FOR | AGCA ACTAGT ACC ATG GCC CTT ATA CTA GTT (SEQ ID NO: 5) |

TABLE 2-continued

Primers used for GST-PI3-Kα PCR Amplification

| Primer Name | Primer Sequence |
|---|---|
| PI3_Ka_REV_GATE | GGGG AC CAC TTT GTA CAA GAA AGC TGG GTG AAGCTT TCA GTT CAA AGC ATG CTG CTT AAT (SEQ ID NO: 6) |

Positive recombinant plasmids containing both GST-PI3-Kα and the truncated p85 adaptor proteins (bovGST-PI3-Kα/p85 pFastbac DUAL) are then confirmed by restriction digest analysis and sequence verified (SOLVIAS).

The RefSeq accession numbers for bovine PIK3CA (p110α) and human PIK3R1 (p85α Isoform 1) are NM_174574.1 and NM_181523, respectively.

The primary sequence of all constructs derived from PCR are confirmed by sequencing through Solvias AG, Basel.

PCR amplifications: PCR-amplifications is performed with a MJ-Research DNA Engine PTC-200 thermal cycler in 100 µl total volume with Pwo Master (Roche).

The full length adaptor protein p85α (PIK3R1, 1-724 aa) is amplified from ing of plasmid pCMV6_XL5::p85α Isoform 1 (Catalog no. TC11320, Origene) with the final concentration of 500 nM of either primer, 1× Master Mix, 5% DMSO and the following primers:

```
p85upnew:
                              (SEQ ID NO: 7)
5'-CCGCGGATCCACCATGAGTGCTGAGGGGTACCAG-3',
and p85do:
                              (SEQ ID NO: 8)
5'-GCCGGAATTCTCATCGCCTCTGCTGTGCATATAC-3'.
```

Cycling parameters are: 94° C., 2 min; (94° C., 15 sec; 53° C., 30 sec; 72° C., 60 sec)$_{10}$; (72° C., 60 sec+5 sec/cycle))$_{19}$; 72° C., 7 min.

The primers p85upnew and p85do introduce the restriction enzyme sites for BamHI and EcoRI at the N-terminus and the C-terminus, respectively.

Cloning:

Cloning of p85 Alpha Isoform 1 (PI3KR1) in pFastBac1

The baculovirus vector pFastBac1 (Invitrogen) and the amplified p85α Isoform 1 DNA are cut with BamHI and EcoRI and are gel-purified. The ligation is performed for 1 hour at room temperature and competent E. coli DH5α cells are transformed to obtain the plasmid pFastBac::p85α Isoform 1.

Cloning of Catalytic p110 Alpha (PIK3CA) in pFastBac1

The plasmid His-Nativ hPI3k-alpha p85 pDUAL is digested with BamHI and HindIII. The obtained fragment is purified from agarose gels and is ligated for 2 to 4 hour at room temperature into pFastBac1 cut with the same restriction enzymes. Transformation into competent E. coli DH5α cells yield the plasmid pFastBac::p110α.

Mutagenesis

Mutagenesis to generate PI3Kα (p110α) mutant Q859A is performed with the QuikChange II Site-Directed Mutagenesis kit (Stratagene (cat. no 200523) and the oligonucleotides

```
p110Q859Aup
                              (SEQ ID NO: 9)
(5'-GAAATTCTCACACTATAATGGCTATTCAGTGTAAAGG
AGGCCTG-3'),
and p110Q859Ado
                              (SEQ ID NO: 10)
(5'-CAGGCCTCCTTTACACTGAATAGCCATTATAGTGTGA
GAATTTC-3')
following the manufacturer's protocol.
```

Protein Expression:

(a) Virus Generation and Protein Expression

Recombinant baculovirus DNA is generated by transposition in E. coli DH10 Bac (Invitrogen). Bacmid DNA is isolated from single colonies and then is transfected into Sf9 cells. Transfections, amplifications, and plaque assays are performed according to the manual of the Bac-to-Bac Baculovirus Expression System (Invitrogen) in TC-100 medium (Cambrex) supplemented with 10% FCS. Virus titers are determined by standard plaque assays. Expression is done in shake flasks starting from 1×10$^6$ cells/ml in ExCell-420 medium (JRH Biosciences Ltd) supplemented with 0.5× Penicillin/Streptomycin solution (Sigma).

In order to reconstitute the active holo-enzyme of the catalytic subunit p110 and adaptor protein p85 during expression Sf9 cells are co-infected with both viruses simultaneously. Proteins are expressed in 100 ml culture medium for 72 h at 27° C. following the TIPS protocol as described elsewhere (e.g., Erdmann et al (2010), J. Biomol. Tech.; 21(1):9-17). The relative co-infection ratio of p110 to p85 is varied and the optimal co-infection ratio is 1:1. The protein expression is visualized by examining whole-cell lysates by Western-blotting. Solubility of the PI3Kα protein is high (85-90% soluble).

Protein Purification:

Recombinant proteins are purified from baculovirus-infected Sf9 insect cells. About 1.5×10$^8$ cells from one 100 ml fermentation are re-suspended in 12 ml lysis buffer (50 mM Tris pH=7.2, 150 mM NaCl, 1 mM MgCl$_2$, 1 mM CaCl$_2$, 1% Triton X-100, 10% glycerol, 6 µl Benzonase (25 U/µl), 1× Complete protease inhibitor (Roche), 1 mM activated sodium orthovanadate) and are disrupted by sonication (Branson Digital sonifier W-450D for a total of 3 minutes in ice/ethanol bath (pulses 30 sec, cooling 1 min. between pulses). Cell debris is removed by centrifugation at 14000×g (Sorvall centrifuge RC5-B, SS-34 rotor, 11000 rpm, 45 min. at 4° C.) and the supernatant is transferred to a new tube.

For histidine-affinity tag purification of p110α/p85α 1 ml His-Trap HP Ni-sepharose columns (cat. no. 17-5247-01, GE Healthcare) attached to an Äkta explorer FPLC system are used. Columns are equilibrated with 25 mM Tris-HCl pH 7.5, 0.5 M NaCl and the cleared lysates are loaded with a superloop at a flow rate of 0.5 ml/min. After washing with 10 CV of 25 mM Tris-HCl pH=7.5, 0.5 M NaCl, 25 mM imidazole, the bound protein is eluted with a stepwise imidazole gradient of 50, 60, 70, 80, 90, 100, 125, 150, 250, and 500 mM imidazole. Eluted protein is concentrated about 10-fold via centrifugation with Amicon Ultra-15 spin-columns and, after adding glycerol to final 30% (v/v), is aliquoted and snap-frozen in liquid nitrogen.

The protein concentration is determined in duplicates with BCA Protein Assay Kit (cat. no. 23227, Pierce) in microtiter plates following the protocol provided with the kit.

Materials and Methods for Enzymatic HTRF® Assay

The Phosphoinositide 3-kinase (PI3-Kinase or PI3K) Homogenous Time-Resolved (HTRF®) assay kit is purchased from Upstate (now Millipore Corporation, Billerica, Mass., USA). PIP2 and PiP3 is purchased from Avanti Polar Lipids (Alabaster, Ala., USA), microplates from Greiner (Frickenhausen, Germany; Catalog No. 781207). All other reagents are purchased from Sigma (St Louis, Mo., USA).

The enzymatic Homogenous Time-Resolved Fluorescence (HTRF®) assay (from Upstate (now Millipore Corporation, Billerica, Mass., USA) is performed essentially as described by Sugita et al. (2008), Biochem. Biophys. Res. Commun 377(3):941-5. PI3Kα (0.25-1.5 ng) is incubated for 60 minutes at room temperature in 20 µl buffer containing 10 mM MgCl$_2$, 30 µM ATP, 20 µM 1,2-dioctanoyl-sn-glycero-3-phospho-(1'-myo-inositol-4',5'-bisphosphate) (ammonium salt) (PIP2), 150 mM NaCl, 5 mM (dl-Dithiothreitol) DTT, and 25 mM Tris/HCl (pH 7.5) in 384-well white plates. The kinase reaction is initiated by adding ATP (30 µM) for inhibition studies and by adding PI3Kα for ATP kinetics (0-200 µM ATP).

PI3K inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (hereinafter "Compound I") is diluted successively in Dimethyl sulfoxide (DMSO) and in buffer (final concentration: 2.5% DMSO). The kinase reaction is stopped by addition of the HTRF reagents according to manufacturer's instructions. The plate is sealed to prevent evaporation and is kept in the dark at room temperature for 16 hours. The plate is read using Tecan's GeniosPro® multilabel reader (from Tecan Group Ltd., Männedorf, Switzerland) in time-resolved fluorescence mode (Excitation filter: 340 nm; Emission filter 1: 620 nm; Emission filter 2: 665 nm; Mirror: dichroic2; Lag time: 150 µs; Integration time: 500 µs; 10 flashes).

The HTRF signal is determined according to the formula:

HTRF signal=10000×(emission at 665 nm/emission at 620 nm).

The HTRF signal is gradually decreased in a PIP3 dependent manner and is normalized as % of the maximal decrease obtained with 30 µM 1,2-dioctanoyl-sn-glycero-3-phospho-(1'-myo-inositol-3',4',5'-trisphosphate) (ammonium salt) (PIP3). A standard curve is prepared with PIP3 (EC$_{50}$=200 nM) and is used to calculate the amount of PIP3 produced by the kinase reaction according to the formula:

[PIP3]=EC$_{50}$×(100−y)/y where y represents the normalized HTRF signal and EC$_{50}$ the PIP3 concentration at 50% signal in the standard curve. ATP and PIP2 consumption is never exceeding 5%.

ATP kinetics are fitted by nonlinear regression with the Michaelis-Menten equation and Compound I inhibition curves are fitted with the 4-parameter logistic equation. The global fit function of Xlfit® (ID Business Solutions, Guildford, UK) is used to fit globally all replicate experiments.

Figure 2:
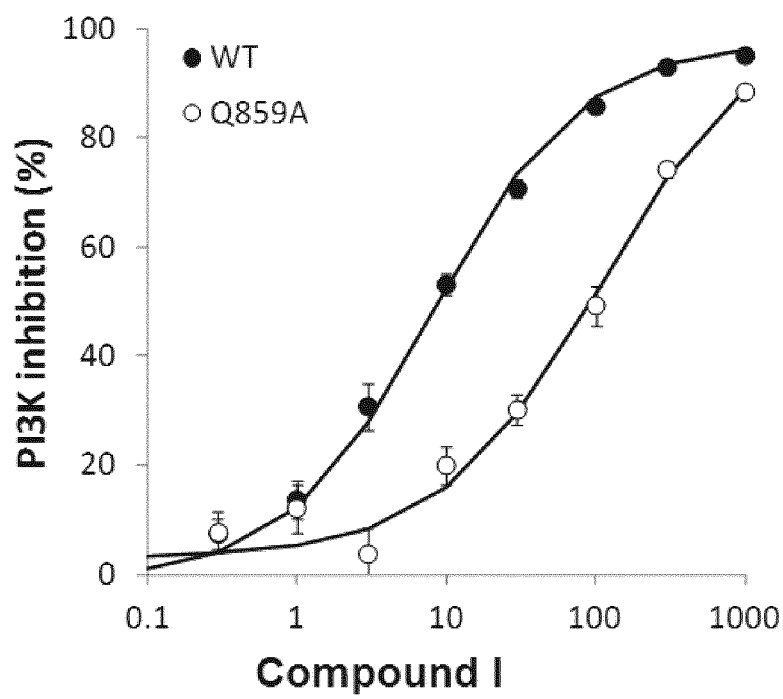
FIG. 2 shows a graph showing the inhibition curves for PI3K wild-type (wt) and for PI3Kα Q859A mutant.

Results:

Using the materials and methods above, the experiments demonstrate the ATP activation kinetics of PI3Kα as set forth in FIG. 1 and the inhibition of PI3Kα wildtype (wt) and Q859A mutation by Compound I as set forth in FIG. 2.

FIG. 1 provides the Mean values±Standard error (S.E.) of 14 experiments for PI3K wild-type (wt) (Michaelis constant (Km)=60±6 µM) and 5 experiments for PI3Kα Q859A mutant (Km=72±8 µM). As summarized in FIG. 1 hereto, the PI3K wild-type (wt) and PI3Kα Q859A mutant demonstrate similar ATP activation kinetics of PI3Kα.

FIG. 2 provides the Mean Values±Standard Error (S.E.) of 10 experiments for PI3K wild-type (wt) and 7 experiments for PI3Kα Q859A mutant. As summarized in FIG. 2 hereto, the mutation of Q859A in PI3Kα significantly increases the IC$_{50}$ to 122±28 nM as compared to wildtype (IC$_{50}$=8.4±1.0 nM). This 14.5-fold increase in the IC$_{50}$ to 122±28 nM clearly demonstrates that the mutation of Q859 in PI3Kα is a key residue to assess the potency of Compound I upon administration.

---

What is claimed is:

1. A method of selectively treating a subject having breast cancer, a tumor of the head and neck, kidney cancer, or pancreatic cancer, comprising:
   a) assaying a biological sample from the subject for the presence or absence of a glutamine at position 859 of the catalytic p110α subunit of PI3K, and selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, to the subject on the basis that the sample has a glutamine at position 859;
   or
   b) assaying a biological sample from the subject for the presence or absence of a nucleic acid sequence that encodes a glutamine at position 859 of the catalytic p110α subunit of PI3K, and selectively administering a therapeutically effective amount of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, to the subject on the basis that the sample has a nucleic acid sequence that encodes a glutamine at position 859.

2. A method of selectively treating a subject having breast cancer, a tumor of the head and neck, kidney cancer, or pancreatic cancer, comprising:
   a) assaying a biological sample from the subject for the presence or absence of nucleic acid sequence mutation in the catalytic p110α subunit of PI3K, wherein the mutation results in an amino acid substitution of glutamine at position 859 of the catalytic p110α subunit of PI3K;
   b) thereafter selecting the subject for treatment with (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide), or a pharmaceutically acceptable salt thereof, on the basis that the sample from the subject lacks the mutation and encodes glutamine at position 859 of the catalytic p110α subunit of PI3K; and
   c) thereafter administering (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof to the subject lacking the mutation.

* * * * *

SEQUENCE LISTING

```
<160> NUMBER OF SEQ ID NOS: 10

<210> SEQ ID NO 1
<211> LENGTH: 1068
<212> TYPE: PRT
<213> ORGANISM: homo sapiens

<400> SEQUENCE: 1

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125
```

```
Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
                180                 185                 190

Val Ile Trp Val Ile Val Ser Pro Asn Asn Asp Lys Gln Lys Tyr Thr
            195                 200                 205

Leu Lys Ile Asn His Asp Cys Val Pro Glu Gln Val Ile Ala Glu Ala
    210                 215                 220

Ile Arg Lys Lys Thr Arg Ser Met Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
                260                 265                 270

Ile Arg Ser Cys Ile Met Leu Gly Arg Met Pro Asn Leu Met Leu Met
            275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
                340                 345                 350

Lys Ile Tyr Val Arg Thr Gly Ile Tyr His Gly Gly Glu Pro Leu Cys
            355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
                420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
                500                 505                 510

Leu Ser Asn Arg Leu Ala Arg Asp Asn Glu Leu Arg Glu Asn Asp Lys
            515                 520                 525

Glu Gln Leu Lys Ala Ile Ser Thr Arg Asp Pro Leu Ser Glu Ile Thr
    530                 535                 540
```

-continued

```
Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
```

|   |   |   | 965 |   |   | 970 |   |   | 975 |   |   |
|---|---|---|---|---|---|---|---|---|---|---|---|

Phe Glu Arg Phe Gln Glu Met Cys Tyr Lys Ala Tyr Leu Ala Ile Arg
            980            985            990

Gln His Ala Asn Leu Phe Ile Asn Leu Phe Ser Met Met Leu Gly Ser
      995            1000           1005

Gly Met Pro Glu Leu Gln Ser Phe Asp Asp Ile Ala Tyr Ile Arg
  1010           1015           1020

Lys Thr Leu Ala Leu Asp Lys Thr Glu Gln Glu Ala Leu Glu Tyr
  1025           1030           1035

Phe Met Lys Gln Met Asn Asp Ala His His Gly Gly Trp Thr Thr
  1040           1045           1050

Lys Met Asp Trp Ile Phe His Thr Ile Lys Gln His Ala Leu Asn
  1055           1060           1065

<210> SEQ ID NO 2
<211> LENGTH: 3207
<212> TYPE: DNA
<213> ORGANISM: Homo sapiens

<400> SEQUENCE: 2

| | |
|---|---|
| atgcctccac gaccatcatc aggtgaactg tggggcatcc acttgatgcc cccaagaatc | 60 |
| ctagtagaat gtttactacc aaatggaatg atagtgactt tagaatgcct ccgtgaggct | 120 |
| acattaataa ccataaagca tgaactattt aaagaagcaa gaaataccc cctccatcaa | 180 |
| cttcttcaag atgaatcttc ttacattttc gtaagtgtta ctcaagaagc agaaagggaa | 240 |
| gaatttttg atgaaacaag acgactttgt gaccttcggc ttttttcaacc cttttttaaaa | 300 |
| gtaattgaac cagtaggcaa ccgtgaagaa aagatcctca atcgagaaat tggttttgct | 360 |
| atcggcatgc cagtgtgtga atttgatatg gttaaagatc cagaagtaca ggacttccga | 420 |
| agaaatattc tgaacgtttg taagaagct gtggatctta gggacctcaa ttcacctcat | 480 |
| agtagagcaa tgtatgtcta tcctccaaat gtagaatctt caccagaatt gccaaagcac | 540 |
| atatataata aattagataa agggcaaata atagtggtga tctgggtaat agtttctcca | 600 |
| aataatgaca agcagaagta tactctgaaa atcaaccatg actgtgtacc agaacaagta | 660 |
| attgctgaag caatcaggaa aaaaactcga agtatgttgc tatcctctga caactaaaa | 720 |
| ctctgtgttt tagaatatca gggcaagtat attttaaaag tgtgtggatg tgatgaatac | 780 |
| ttcctagaaa aatatcctct gagtcagtat aagtatataa gaagctgtat aatgcttggg | 840 |
| aggatgccca atttgatgtt gatggctaaa gaaagccttt attctcaact gccaatggac | 900 |
| tgttttacaa tgccatctta tccagacgc atttccacag ctacaccata tgaatgga | 960 |
| gaaacatcta caaatccct tgggttata aatagtgcac tcagaataaa aattctttgt | 1020 |
| gcaacctacg tgaatgtaaa tattcgagac attgataaga tctatgttcg aacaggtatc | 1080 |
| taccatggag gagaaccctt atgtgacaat gtgaacactc aaagagtacc ttgttccaat | 1140 |
| cccaggtgga atgaatggct gaattatgat atatacattc tgatcttcc tcgtgctgct | 1200 |
| cgactttgcc tttccatttg ctctgttaaa ggccgaaagg gtgctaaaga ggaacactgt | 1260 |
| ccattggcat gggaaatat aaacttgttt gattacacag acactctagt atctggaaaa | 1320 |
| atggctttga atctttggcc agtacctcat ggattagaag atttgctgaa ccctattggt | 1380 |
| gttactggat caaatccaaa taagaaaact ccatgcttag agttggagtt tgactggttc | 1440 |
| agcagtgtgg taaagttccc agatatgtca gtgattgaag agcatgccaa ttggtctgta | 1500 |
| tcccgagaag caggatttag ctattcccac gcaggactga gtaacagact agctagagac | 1560 |

```
aatgaattaa gggaaaatga caaagaacag ctcaaagcaa tttctacacg agatcctctc    1620
tctgaaatca ctgagcagga gaaagatttt ctatggagtc acagacacta ttgtgtaact    1680
atccccgaaa ttctacccaa attgcttctg tctgttaaat ggaattctag agatgaagta    1740
gcccagatgt attgcttggt aaagattgg cctccaatca aacctgaaca ggctatggaa     1800
cttctggact gtaattaccc agatcctatg gttcgaggtt ttgctgttcg gtgcttggaa    1860
aaatatttaa cagatgacaa actttctcag tatttaattc agctagtaca ggtcctaaaa    1920
tatgaacaat atttggataa cttgcttgtg agatttttac tgaagaaagc attgactaat    1980
caaaggattg ggcactttt cttttggcat ttaaaatctg agatgcacaa taaaacagtt     2040
agccagaggt ttggcctgct tttggagtcc tattgtcgtg catgtgggat gtatttgaag    2100
cacctgaata ggcaagtcga ggcaatggaa aagctcatta acttaactga cattctcaaa    2160
caggagaaga aggatgaaac acaaaaggta cagatgaagt ttttagttga gcaaatgagg    2220
cgaccagatt tcatggatgc tctacagggc tttctgtctc ctctaaaccc tgctcatcaa    2280
ctaggaaacc tcaggcttga agagtgtcga attatgtcct ctgcaaaaag gccactgtgg    2340
ttgaattggg agaacccaga catcatgtca gagttactgt ttcagaacaa tgagatcatc    2400
tttaaaaatg gggatgattt acggcaagat atgctaacac ttcaaattat tcgtattatg    2460
gaaaatatct ggcaaaatca aggtcttgat cttcgaatgt taccttatgg ttgtctgtca    2520
atcggtgact gtgtgggact tattgaggtg gtgcgaaatt ctcacactat tatgcaaatt    2580
cagtgcaaag gcggcttgaa aggtgcactg cagttcaaca gccacacact acatcagtgg    2640
ctcaaagaca agaacaaagg agaaatatat gatgcagcca ttgacctgtt tacacgttca    2700
tgtgctggat actgtgtagc taccttcatt ttgggaattg gagatcgtca caatagtaac    2760
atcatggtga aagacgatgg acaactgttt catatagatt ttggacactt tttggatcac    2820
aagaagaaaa aatttggtta taacgagaaa cgtgtgccat tgttttgac acaggatttc     2880 ttaatagtga ttagtaaagg agcccaagaa tgcacaaaga caagagaatt tgagaggttt    2940
caggagatgt gttacaaggc ttatctagct attcgacagc atgccaatct cttcataaat    3000
cttttctcaa tgatgcttgg ctctggaatg ccagaactac aatcttttga tgacattgca    3060
tacattcgaa agaccctagc cttagataaa actgagcaag aggctttgga gtatttcatg    3120
aaacaaatga atgatgcaca tcatggtggc tggacaacaa aaatggattg gatcttccac    3180
acaattaaac agcatgcatt gaactga                                       3207
```

```
<210> SEQ ID NO 3
<211> LENGTH: 70
<212> TYPE: DNA
<213> ORGANISM: Artificial Sequence
<220> FEATURE:
<223> OTHER INFORMATION: Primer

<400> SEQUENCE: 3
ggggacaagt ttgtacaaaa aagcaggctg gggatccacc atgcctccaa gaccatcatc    60
aggtgaactg                                                          70

<210> SEQ ID NO 4
<211> LENGTH: 60
<212> TYPE: DNA
<213> ORGANISM: Artificial Sequence
<220> FEATURE:
<223> OTHER INFORMATION: Primer
```

<400> SEQUENCE: 4
ggggaccact tgtacaaga aagctgggtg aagctttcag ttcaaagcat gctgcttaat    60

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
agcaactagt accatggccc ttatactagt t    31

<210> SEQ ID NO 6
<211> LENGTH: 60
<212> TYPE: DNA
<213> ORGANISM: Artificial Sequence
<220> FEATURE:
<223> OTHER INFORMATION: Primer

<400> SEQUENCE: 6
ggggaccact tgtacaaga aagctgggtg aagctttcag ttcaaagcat gctgcttaat    60

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
ccgcggatcc accatgagtg ctgaggggta ccag    34

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
gccggaattc tcatcgcctc tgctgtgcat atac    34

<210> SEQ ID NO 9
<211> LENGTH: 44
<212> TYPE: DNA
<213> ORGANISM: Artificial Sequence
<220> FEATURE:
<223> OTHER INFORMATION: Primer

<400> SEQUENCE: 9
gaaattctca cactataatg gctattcagt gtaaaggagg cctg    44

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
caggcctcct ttacactgaa tagccattat agtgtgagaa tttc    44